United States Patent [19]

Halm et al.

[11] Patent Number: 4,962,220

[45] Date of Patent: Oct. 9, 1990

[54] METHOD FOR PREPARING ORGANOHALOSILANES

[75] Inventors: Roland L. Halm, Madison, Ind.; Regie H. Zapp, Carrollton, Ky.

[73] Assignee: Dow Corning Corporation, Midland, Mich.

[21] Appl. No.: 459,483

[22] Filed: Jan. 20, 1990

[51] Int. Cl.$^5$ .............................................. C07F 7/16
[52] U.S. Cl. ................................................... 556/473
[58] Field of Search ...................................... 556/473

[56] References Cited

U.S. PATENT DOCUMENTS

| | | | |
|---|---|---|---|
| 2,380,996 | 8/1945 | Rochow et al. | 556/473 X |
| 2,380,997 | 8/1945 | Patnode . | |
| 2,380,999 | 8/1945 | Sprung et al. . | |
| 2,383,818 | 8/1945 | Rochow et al. . | |
| 2,595,620 | 5/1952 | Wagner et al. | 556/473 X |
| 2,917,529 | 12/1959 | Drysdale | 556/473 X |
| 3,109,014 | 10/1963 | Tamura et al. . | |
| 4,500,724 | 2/1985 | Ward, III et al. . | |

FOREIGN PATENT DOCUMENTS 1089726  9/1966  U.S.S.R. .............................. 556/473

OTHER PUBLICATIONS

Csakvari, et al., Acta Chim. Hung., Acad. Sci. Hung., 39 (1), 33-7 (1963), "Direct Synthesis of Methylchlorosilanes, II".
Golubtsov, et al., Zh. Prikl. Khim. Leningrad (J. Applied Chemistry) (1964), 37(7) 1634, 1623 CB.
Rathousky, et al., (1972).
De Cooker, et al., J. Org. Chem. 99 (1975) 371-377.
Morozova, et al., No. 6, pp. 1005-1011, Jun. 1962, Izvestiya Akademii.
Nauk SSSR, Otdelenie Khimicheskikh Nauk, Gorbunov, et al., Doklady Adademii Nauk SSSR, vol. 194, No. 1, pp. 92-94, Sept. 1970.
Joklik, et al., XXXIII, Mitteilung: Diese Zeitschrift 29,603 (1964), pp. 834-837.
Andrianov, et al., Izvestiya Akademii Nauk SSSR, No. 10, pp. 1788-1794, Oct. 1962.

*Primary Examiner*—Paul F. Shaver
*Attorney, Agent, or Firm*—Robert Spector

[57] ABSTRACT

The present invention provides a method for reducing the concentration of methyltrichlorosilane in the mixture of methylchlorosilanes obtained from the direct process reaction of silicon metal with a mixture of methyl chloride and hydrogen chloride. The method comprises blending the methyl chloride/hydrogen chloride mixture with from 0.1 up to about 5 weight percent of hydrogen, based on the methyl chloride.

6 Claims, No Drawings

METHOD FOR PREPARING ORGANOHALOSILANES

BACKGROUND OF THE INVENTION

1. Field of the Invention

This invention relates to the preparation of organohalosilanes. More particularly, this invention relates to a method for increasing the yield of monoorganodichlorosilanes and/or reducing the yield of undesired monoorganotrichlorosilanes using a method referred to in the art as the "direct process" without either adversely affecting the yield of other desirable organochlorosilanes, particularly the combined yield of monoorganodichlorosilane and the corresponding diorganodichlorosilane, or generating substantial quantities of undesirable inorganic halosilanes and organotrihalosilanes.

2. Description of Relevant Art

The preparation of organohalosilanes by the reaction of an alkyl or aryl halide with silicon metal in the presence of various catalysts is known as the "direct process". The halide portion is typically chlorine, but can also be bromine or iodine.

Preparing halosilanes by reacting silicon with hydrogen chloride has been known since the work of Buff and Wöhler in 1857 and Combes in 1896. Application of the direct process to the preparation of organohalosilanes was first disclosed by Rochow and his co-workers, beginning in the mid-1940's. The art describes numerous improvements to this direct process.

Rochow and Patnode, U.S. Pat. No. 2,380,996, issued Aug. 7, 1945, and Patnode, U.S. Pat. No. 2,380,997, issued Aug. 7, 1945, disclose the preparation of a contact mass for the direct process. The mass is prepared by firing a mixture of silicon, copper, or other metallic catalysts in a reducing atmosphere. Rochow and Patnode and Patnode also disclose the use of nickel, tin, antimony, manganese, silver, and titanium.

Rochow and Gilliam, U.S. Pat. No. 2,383,818, issued Aug. 28, 1945, discloses the use of contact masses comprising silicon and an oxide of copper. Also, included are copper compounds which are readily converted to the oxides, such as copper nitrate. An example of more recent art is Chapters 4 and 5 of a text entitled Organohalosilanes by R. J. H. Voorhoeve, published in 1967 by Elsevler.

For various reasons, including cost and availability of starting materials, alkylchlorosilanes, particularly methyl- and ethylchlorosilanes, have become the organohalosilanes most frequently prepared by the direct process. The present invention has therefore been limited to this class of alkylchlorosilanes using the corresponding alkyl chlorides. It should be understood that while preferred embodiments of the present invention are directed Primarily to the preparation of certain methylchlorosilanes by reacting methyl chloride and silicon, the invention is not to be so limited.

When methyl chloride, represented by the formula MeCl, and silicon metal are reacted using the catalysts and reaction conditions described in the prior art, the resultant products include but are not limited to MeHSiCl$_2$, Me$_2$SiCl$_2$, Me$_3$SiCl, MeSiCl$_3$, Me$_2$HSiCl, HSiCl$_3$ and SiCl$_4$, where Me represents the methyl radical. By an appropriate selection of catalyst and reaction conditions it is possible to obtain dimethyldichlorosilane, Me$_2$SiCl$_2$, as the major component, often 90 weight % or more, in the final product mixture. Methyldichlorosilane, MeHSiCl$_2$ typically constitutes about 1 weight percent of the product under these conditions, which are designed to optimize the yield of Me$_2$SiCl$_2$. The reaction product also typically contains a significant concentration of methyltrichlorosilane, MeSiCl$_3$, which in many instances is not a desired product.

The prior art provides no teaching to enable one to increase the relative concentration of methyldichlorosilane in a direct process product mixture without either a substantial decrease in the combined yield of this product and dimethyldichlorosilane or producing substantial amounts of undesirable products, particularly methyltrichlorosilane and carbon. Carbon is especially undesirable because it collects on the silicon reaction mass and may decrease the rate of the methyl chloride/silicon reaction or cause it to stop all together.

The art teaches combining the methyl chloride with 5 weight percent or more, based on methyl chloride, of hydrogen as a means for increasing the relative yield of methyldichlorosilane in the final product, however the yield of dimethyldichlorosilane is more than correspondingly reduced and substantial quantities of undesirable organic halosilanes are produced.

For example, U.S. Pat. No. 2,380,999 which issued to Sprung et al. on Aug. 7, 1945 teaches sintering a mixture containing 90 weight percent silicon and 10 weight percent copper for one hour at 1050° C. under a hydrogen atmosphere. The resultant reaction mass is then placed in a stream of ethyl chloride flowing at a rate of 80 cc. per minute. Following separation of volatile materials the liquid reaction product was found to contain 73.5 weight percent dimethyldichlorosilane, 9 percent methyltrichlorosilane, 6 weight percent trimethylchlorosilane, and "small amounts of other methylchlorosilanes". Combining the methyl chloride with nitrogen increased the yield of dimethyldichlorosilane to 86.5 percent, the only other specifically reported product being 4.0 weight percent of methyltrichlorosilane.

An article by Csakvari et al. that appeared in Acta Chim. Acad. Sci. Hung. 39 (1), 33–7 (1963) mentions prior art disclosing the use of methyl chloride/hydrogen mixtures to achieve a 20 weight percent yield of methyldichlorosilane in the final product. The types and amounts of other methylchlorosilanes produced are not disclosed.

British patent no. 1,089,726, which issued to Morozov et al. on Nov. 8, 1967 teaches obtaining up to a 65 weight percent yield of methyldichlorosilane, based on total reaction product, or up to a 16 weight percent yield of dimethylchlorosilane by adding iron, cobalt, nickel, or their salts to the silicon/copper reaction mass in a direct process and blending the methyl chloride with hydrogen. The rates of addition of hydrogen and methyl chloride are each from 0.1 to 0.5 liters per minute. The products described in the examples of this patent contain from 13 to 33 weight percent of methyltrichlorosilane.

An article by J. Rathousky et al. [Chem. Prum., 22(10), 485–8 (1972) discusses the effect of hydrogen addition on a direct process reaction of methyl chloride with a 9:1 weight ratio mixture of silicon and copper under superatmospheric pressure at a temperature of 320° C. The yield of methyldichlorosilane increased by a factor of 5 and the yield of dimethyldichlorosilane decreased proportionately as the hydrogen concentration was increased from 0 to 15 mole percent of a methyl chloride/hydrogen mixture. The yield of methyltrichlorosilane remained substantially constant over the range of hydrogen concentrations investigated. The combination of methyldichlorosilane and dimethyldichlorosilane amounted to about 60 weight percent of the reaction product at all hydrogen concentrations, and the reaction product contained small amounts of dichlorosilane, trichlorosilane, silicon tetrachloride and trimethylchlorosilane.

The effect of varying amounts of hydrogen on the direct process reaction using a copper catalyst is reported by M. De Cooker et al. in the Journal of Organometallic Chemistry, 99(1975) 371–377. During the 5 experimental runs the partial pressure of hydrogen was varied from 0.55 to 0.75 atmosphere, and the combined pressure of hydrogen and the methyl chloride reactant totaled one atmosphere. The highest yield of dimethyldichlorosilane reported is 88 mole percent, and the corresponding yields of methyldichlorosilane and trimethylchlorosilane were 4 mole percent each.

The prior art also teaches combining the methyl chloride with 5 weight percent or more, based on methyl chloride, of hydrogen chloride as a means for increasing the relative yield of methyldichlorosilane in the final product, however the yield of dimethyldichlorosilane is more than correspondingly reduced and substantial quantities of undesirable inorganic halosilanes are produced. For example, U.S. Pat. No. 3,454,616, which issued to Ariga et al. on July 8, 1969 teaches reacting silicon metal with mixtures of methyl chloride and from 20 to 83 percent, based on the weight of the mixture, of hydrogen chloride. In accordance with the examples of this patent, when these gaseous mixtures are reacted with metallic silicon containing catalytic amounts of copper and nickel the reaction product contains up to 36 weight percent of methyldichlorosilane.

Depending upon reaction conditions and the molar ratio of hydrogen chloride to methyl chloride, the reaction product also contained from 2.4 to 32.5 weight percent of dimethyldichlorosilane. The product also contained traditionally undesirable products, including from 5.6 to 33 weight percent of trichlorosilane, from 14.6 to 25.2 weight percent of methyltrichlorosilane and from 0.6 to 2.3 weight percent of silicon tetrachloride.

The addition of aluminum chloride or boron trichloride in catalytic amounts to increase the amount of methyl-dichlorosilane formed by the reaction of methyl chloride and hydrogen chloride with silicon metal is taught in U.S. Pat. No. 3,109,014, which issued to Tamura et al. on Oct. 29, 1963. As in the Ariga et al. patent, excessive amounts of the undesirable inorganic halosilanes are produced.

Golubsov et al. report in the Journal of Applied Chemistry, Russian edition, 37 (7), p. 1634 (1964) that the presence of hydrogen chloride increases the yield of phenyltrichlorosilane from the reaction of chlorobenzene and silicon metal. A product containing 55 mole percent of phenyltrichlorosilane and only 0.7 mole percent of phenyldichlorosilane is reportedly obtained from the reaction of a silicon alloy with a mixture of chlorobenzene and hydrogen chloride containing 62 weight percent of hydrogen chloride. The yield of diphenyldichlorosilane is not disclosed.

L. Morozov et al. [Izvestia Akaademii Nauk SSSR Ser. Kim. (1962) (6) 941] reacted a mixture of silicon and catalytic amounts of copper oxide, zinc oxide and sodium silicate with a mixture of methyl chloride and 5 or 10 percent by volume of hydrogen chloride at a temperature of 350° C. Five volume percent of hydrogen chloride produced 43 weight percent of methyldichlorosilane, 2 percent of dimethyldichlorosilane, 31 percent of methyltrichlorosilane, and 6 weight percent of silicon tetrachloride. Ten volume percent of hydrogen chloride yielded 42 weight percent of methyldichlorosilane, 8 percent of methyldichlorosilane and 9 percent of silicon tetrachloride.

The data in an article by Gorbunov et al. in the September 1970 issue of Doklady Akademi Nauk. SSR. 194, 1 (92–94) demonstrate that 35 weight percent of methyldichlorosilane, only about 10 weight percent of dimethyldichlorosilane with about the same amount of silicon tetrachloride is obtained by reacting silicon with a 3:1 weight ratio mixture of methyl chloride and hydrogen chloride at 300 degrees C.

J. Joklik et al. [Collect. Czech. Chem. Commun. (1964) 29(3) 834] disclose reacting silicon with various ratios of methyl chloride to hydrogen chloride in the presence of a copper catalyst at temperatures of 260°, 300°, and 350° C. At 260° C. as the mole ratio of hydrogen chloride to methyl chloride in the reactor was stream was increased from 1:6 to 1:1 the weight percent of methyldichlorosilane in the reaction product increased from 8.9 to 14 percent while the yield of trichlorosilane increased from 4.3 to 15 percent and the yield of methyltrichlorosilane increased from 15.5 to 32.9 weight percent. At 350° C. using a 1:6 mole ratio of hydrogen chloride to methyl chloride in the reactor gas stream the yield of methyldichlorosilane was 6.5 weight percent, while the yields of undesirable methyltrichlorosilane, trichlorosilane and silicon tetrachloride were 35.3, 0.4 and 0.3 percent by weight, respectively. When the mole ratio of hydrogen chloride to methyl chloride was 2:3 the reaction product contained 14.1 weight percent of methyldichlorosilane, 52.4 weight percent of methyltrichlorosilane 2.9 percent of trichlorosilane and 1.2 percent of silicon tetrachloride.

Finally, the effect of diluting ethyl chloride with various levels of hydrogen chloride was reported on by Andrianov et al. in Izvestiya Akademii Nauk SSSR (Chemical Section) 10, 1788–1794 (1962). Reacting a mixture of 92 weight percent ethyl chloride and 8 percent hydrogen chloride yielded a mixture of chlorosilanes containing 30 percent by weight of trichlorosilane, 12 percent of $SiCl_4$, 8.8 percent of ethyldichlorosilane and 50 percent of diethyldichlorosilane.

Methods for increasing the yields of dimethyldichlorosilane while reducing the yield of methyltrichlorosilane obtained using the direct process are described in the prior art. For example, U.S. Pat. No. 4,500,724, which issued to Ward et al. on Feb. 19, 1985 teaches using specified mixtures of copper, zinc and tin to increase the yield of dimethyldichlorosilane and reduce the yield of methyltrichlorosilane in a direct process reaction. The weight ratio of methyltrichlorosilane to dimethyldichlorosilane reported in the examples of this patent is from 0.041 to 0.099.

An objective of this invention is to provide a method for increasing the yield of methyldichlorosilane in the direct process without substantially affecting the combined yield of this silane, dimethylchlorosilane and dimethyldichlorosilane or producing excessive amounts of methyltrichlorosilane or inorganic chlorosilanes such as $SiCl_4$ and $SiHCl_3$.

SUMMARY OF THE INVENTION

The present invention is based on the discovery that when small concentrations of hydrogen and hydrogen chloride are blended with the methyl chloride that is reacted with silicon metal to form methylchlorosilanes, the yield of methyldichlorosilane is increased without producing substantial amounts of undesirable methyltrichlorosilane, $SiCl_4$ and/or $SiHCl_3$, or adversely affecting the combined yield of methyldichlorosilane, dimerhylchlorosilane and dimethyldichlorosilane.

DETAILED DESCRIPTION OF THE INVENTION

This invention provides an improvement in the method for increasing the yield of methyldichlorosilane obtained during the production of methylchlorosilanes by the reaction of a gaseous mixture comprising methyl chloride and hydrogen chloride with a reaction mass comprising silicon metal and a suitable catalyst at a temperature of from 50° to about 350° C. The improvement comprises homogeneously blending the methyl chloride and hydrogen chloride with an amount of hydrogen sufficient to reduce the concentration of methyltrichlorosilane in the product of said reaction.

A copending application filed in the names of Roland Halm and Regie Zapp teaches using small amounts of hydrogen chloride in the direct process for preparing alkylchlorosilanes. When less than about 1 weight percent of hydrogen chloride is combined with methyl chloride the concentration of methyldichlorosilane in the reaction product is substantially increase without substantially decreasing the combined yield of this silane and dimethyldichlorosilane. At higher concentrations of hydrogen chloride this process yields relatively large concentrations of methyltrichlorosilane, $SiCl_4$ and $SiHCl_3$, all of which are usually undesirable by-products.

The present inventors discovered that by using a mixture of hydrogen, hydrogen chloride and methyl chloride in the direct process, the beneficial effects of both modifiers can be obtained with a reduction in the disadvantages of each.

In accordance with the present method from 0.02 to 10 weight percent of a mixture of hydrogen chloride and hydrogen, based on methyl chloride, is introduced together with the methyl chloride. Experimental data generated by the present inventors indicate that the hydrogen chloride to hydrogen ratio is not critical, so long as the hydrogen concentration does not exceed 5 percent, based on methyl chloride weight. The hydrogen typically constitutes from 5 to about 90 weight percent of the hydrogen chloride mixture.

The limits for the combined hydrogen/hydrogen chloride concentration are preferably from 0.1 to about 3 percent of the methyl chloride weight, and hydrogen constitutes from 10 to about 60 weight percent of this mixture.

When the present method is conducted in a batch or semi-batch mode the present inventors found it desirable to have more of the hydrogen chloride present during the initial methyl chloride addition, and reduce or eliminate hydrogen chloride during the terminal portion of the methyl chloride addition. In accordance with a particularly preferred embodiment hydrogen chloride is present in only the initial 50 to about 90 weight % of the methyl chloride added to the reactor.

Reaction Conditions and Equipment

The optimum concentration ranges for the hydrogen chloride and hydrogen and the relative concentrations of these gases with respect to one another are at least partially dependent on the type of equipment and reaction conditions used in practicing the present method. Suitable equipment for conducting the direct process include fixed bed, stirred bed and fluid bed reactors. Any of these reactors can be operated in a continuous or batch mode.

It is within the scope of the present invention to utilize the reactor described in U.S. Pat. No. 3,133,109, which issued to Dotson on May 12, 1964 or the one described by Maas et al. in U.S. Pat. No. 4,218,387.

The particle size of the fluidized material should be within the range typically used for the direct process. Dotson in U.S. Pat. No. 3,133,109 discloses particle size range of from 20 to 200 microns. Depending upon the capacity of the reactor, a range of from 1 to 200 microns is preferred for the present method.

The temperature range used for the direct process is typically from 250° to about 350° C. Temperatures within the range of from 260° to about 330° C. are preferred to optimize yields of the desired methylchlorosilanes.

Reaction Catalysts and Promoters

The combination of high yields of dimethyldichlorosilane and dimethylchlorosilane together with a reduction in the concentration of methyltrichlorosilane achieved using the present method is believed due to (1) the mixture of hydrogen chloride, hydrogen and methyl chloride that is reacted with silicon and (2) the presence of a catalyst composition that will suppress the formation of methyltrichlorosilane during this reaction.

Catalysts suitable for use in the present method include but are not limited to copper or a copper compound in combination with at least one of tin and zinc. The tin and zinc can be in the form of the metals or compounds of these metals.

The art pertaining to the direct process for preparing akkylhalosilanes discloses a variety of catalysts and promoters suitable for use in the direct process.

U.S. Pat. No. 4,500,724, which issued to Ward et al. discloses catalysts for the production of organohalosilanes comprising copper and copper oxides, tin or tin-containing compounds, and zinc or zinc-containing compounds. In accordance with the teaching of this patent the concentration of methyltrichlorosilane in a silicon/methyl chloride reaction product is reduced using specified ratios of copper, zinc and tin as the catalyst for the reaction.

Halm et al. in U.S. Pat. No. 4,602,101, issued July 22, 1986, discloses catalysts for controlling product selectivity and increasing silicon conversion during the reaction of an alkyl halide with metallurgical grade silicon at a temperature of 250°–350° C. The catalysts for this reaction are combinations of copper or a copper compound with tin or a tin compound. The reaction mass also contains phosphorous or phosphorous-containing compounds as reaction promoters. The concentration of phosphorus or phosphorus compound is from 25 to 2500 parts by weight per million parts (ppm) of initial reaction mass, the concentration of copper is from 0.2 to 10 weight percent, based on the initial weight of the reaction mass, and the concentration of tin is from 5 to 200 ppm.

The concentration limits on phosphorus, copper and tin disclosed in the aforementioned patent to Halm et al. also apply to the reaction mixtures of the present invention. When zinc is used as a catalyst, it is preferably present at a concentration of present at a concentration of from 10 to 10,000 ppm, based on initial reaction mass. The silicon can also contain up to one weight percent each of aluminum and/or iron.

Additional suitable catalysts and promoters that can be used with copper in combination with tin and/or zinc contain at least one element selected from zinc, calcium, barium, titanium, zirconium, cadmium, lead, bismuth, arsenic nickel, antimony, silver, and cobalt. Any of these promoters can be used in its elemental form or as compounds or alloys that contain the element.

Preferred catalyst/promoter compositions include but are not limited to:

1. (a) Copper or a copper compound and (b) zinc or a zinc compound;
2. (a) Copper or a copper compound, (b) zinc or a zinc compound and (c) tin or a tin compound;
3. (a) Copper or a copper compound, (b) tin or a tin compound, and (c) optionally arsenic or an arsenic compound;
4. (a) Copper in the form of a mixture, alloy or compound, (b) at least one member selected from the group consisting of tin, tin compounds, zinc and zinc compounds, and (c) at least one member selected from the group consisting of phosphorus, phosphorus compounds, metal-phosphorus alloys, and metal phosphides;
5. (a) Copper or a copper compound, (b) tin or a tin compound, (c) arsenic or an arsenic compound, and (d) phosphorus or a phosphorus compound;
6. (a) An alloy of silicon with either iron alone or iron in combination with aluminum, where the concentrations of iron and aluminum are less than one weight percent, based on the weight of initial silicon, (b) copper or at least one copper compound and, optionally, at least one member selected from the group consisting of tin, tin compounds, zinc, zinc compounds, elemental phosphorus, metal phosphides and metal phosphorus alloys; and
7. (a) A mixture of copper and zinc that is present as brass, (b) cuprous chloride, (c) tin or at least one tin compound, and (d) a metal-phosphorus alloy.

The metal portion of any metal-phosphorus alloy or phosphide is preferably aluminum, calcium, copper or zinc.

Those promoters for which concentration ranges are not disclosed in the preceding specification are typically used in amounts as low as several parts per million. Up to 10 weight percent, based on initial reaction mass, of some of these promoters can been used without any adverse effects.

For best results, the purity of the silicon should be at least 95% but less than 100%. A metallurgical grade of silicon is preferred. For optimum results the silicon is in a particulate form.

EXAMPLES

The following examples describe preferred embodiments of the present invention with respect to types and concentrations of reactants, catalysts, promoters, process conditions and equipment and should not be interpreted as limiting the present invention as defined in the accompanying claims. Unless otherwise indicated all parts and percentages in the example are by weight, and all prior art mentioned is incorporated by reference thereto.

GENERAL PROCEDURE

The reactions between silicon and methyl chloride or methyl chloride/hydrogen chloride/hydrogen mixtures was conducted in a fluidized bed reactor of the type described in U.S. Pat. No. 3,133,109 to Dotson. The temperature of the sand bath used to heat the reactor was 315° C. and each heating period, equivalent to the reaction time, was 44 hours in duration.

Metallurgical grade silicon (Globe Metallurgical, Inc. Beverly, Ohio) was employed which contained aluminum (0.22%), calcium (0.046%), and iron (0.34%). The hydrogen and hydrogen chloride used were of 99.999% minimum purity, obtained from Matheson Gas Products, Dayton, Ohio. The methyl chloride and hydrogen were individually metered using calibrated flowmeters. When hydrogen was used the gas streams were combined and passed through a static mixer to ensure proper blending prior to being introduced into the reactor.

The material used as the reaction mass was prepared by blending the following ingredients to homogeneity in a suitable container: 100 parts of silicon, 6.48 parts of cuprous chloride, 600 parts per million (ppm) brass (a 1/1 weight ratio alloy of copper and zinc), 30 ppm tin and 2000 ppm copper phosphorus alloy containing 13.5 weight percent phosphorus. The resultant mixture of ingredients was mixed shaking vigorously for 2 to 3 minutes. This mixture was then charged to the reactor, following which the reactor was closed and placed in the 315° C. sand bath. At this time a stream of nitrogen was passed through the reactor. The sand bath was continuously fluidized to maintain a constant temperature within the reactor.

When the temperature of the reactor reached about 315° C. the nitrogen was replaced with a stream of gaseous methyl chloride as the fluidizing medium. The flow of methyl chloride was continued for 44 hours. When hydrogen was added it was blended with the methyl chloride throughout the entire methyl chloride addition.

The products emerging from the reactor were condensed and collected in previously weighed cold traps. The liquid collected in the traps was then transferred to cooled bottles and then injected into the sample chamber of a gas chromatograph using a previously cooled syringe. The chromatograph was used to determine the types and concentration of reaction products. The product concentrations reported in the following examples represent the average of two runs performed under identical conditions.

EXAMPLE 1

(Control Example)

This example typifies the product distribution obtained in the absence of hydrogen and hydrogen chloride.

The product distributions from two runs performed without the addition of hydrogen or hydrogen chloride were determined and the results were averaged. The averaged values were:

| | |
|---|---|
| Dimethyldichlorosilane (Me$_2$SiCl$_2$) | 92.1% |

-continued

| | |
|---|---|
| Methyldichlorosilane (MeHSiCl$_2$) | 1.3% |
| Total | 93.4% |
| Dimethylchlorosilane (Me$_2$HSiCl) | 0.3% |
| Methyltrichlorosilane (MeSiCl$_3$) | 4.1% |

The remaining material was a mixture of other methylchlorosilanes. There were no detectable amounts of HSiCl$_3$ or SiCl$_4$ present.

EXAMPLE 2 ties of hydrogen chloride, hydrogen and methyl chloride with a silicon-containing reaction mass.

The general procedure described in Example 1 was repeated, with the exception that the weight percentages of hydrogen chloride and hydrogen listed in the following Table 1 were combined with the methyl chloride. These percentages are o based on the weight of methyl chloride.

In one instance hydrogen chloride was added only during the first 22 hours of the 44 hour methyl chloride addition.

TABLE 1

| % HCl | % H$_2$ | % Me$_2$SiCl$_2$ (A) | % MeHSiCl$_2$ (B) | Me$_2$HSiCl (C) | A + B + C | % MeSiCl$_3$ |
|---|---|---|---|---|---|---|
| 0.0 | 0.0 | 92.1 | 1.4 | 0.2 | 93.7 | 4.1 |
| 0.5 | 0.5 | 84.4 | 8.1 | 1.3 | 93.8 | 4.0 |
| 0.5 | 0.7 | 85.7 | 7.1 | 1.2 | 94.0 | 3.8 |
| 0.5 | 1.0 | 81.3 | 10.2 | 1.9 | 93.4 | 4.7 |
| 0.7 | 0.2 | 85.0 | 6.9 | 1.0 | 92.9 | 5.1 |
| 1.0 | 0.5 | 79.5 | 9.7 | 1.4 | 90.4 | 6.9 |
| 1.0 | 1.0 | 76.1 | 12.1 | 1.5 | 89.7 | 7.3 |
| 1.5 | 0.5 | 78.4 | 10.7 | 1.0 | 90.1 | 7.0 |
| 1.0* | 0.5 | 80.2 | 10.4 | 2.2 | 92.8 | 4.1 |

*HCl added during first 22 hours of 44 hours methyl chloride addition (Control Example)

This example demonstrates the high concentration of undesirable methyltrichlorosilane produced together with the increased concentration of methyldichlorosilane when 1.0 weigh percent of hydrogen chloride is added to the methyl chloride. The procedure described in example 1 was repeated, with the exception that 1.0 weight percent of hydrogen chloride was blended with the methyl chloride. The averaged concentration of the reaction products from 2 runs was

| | |
|---|---|
| Me$_2$SiCl$_2$ | 75.0% |
| MeHSiCl$_2$ | 8.9% |
| Total | 83.9% |
| MeSiCl$_3$ | 11.8%, and |
| Me$_2$HSiCl | 0.5% |

EXAMPLE 3

This example demonstrates the effect of hydrogen in reducing the concentration of methyltrichlorosilane produced by reacting a hydrogen chloride/methyl chloride mixture with silicon. The procedure described in example 1 was repeated, with the exception that 0.5 weight percent hydrogen and 1.0 weight percent of hydrogen chloride were blended with the methyl chloride. The average concentrations of four of the principal methylchlorosilanes in the final product were:

| | |
|---|---|
| Me$_2$SiCl$_2$ | 79.6% |
| MeHSiCl$_2$ | 9.7% |
| Total | 89.3% |
| MeSiCl$_3$ | 4.0%, and |
| Me$_2$HSiCl | 1.3% |

The presence of hydrogen increased the yield of methyldichlorosilane by 10% relative to Example 2. More importantly there is almost a three-fold reduction in the amount of methyltrichlorosilane.

EXAMPLE 4

This example discloses the yields of the major methylchlorosilanes obtained by reacting various proper- That which is claimed is:

1. In a method for increasing the yield of methyldichlorosilane obtained during the production of methylchlorosilanes by the reaction of a gaseous mixture comprising methyl chloride and hydrogen chloride with a reaction mass comprising silicon metal and a suitable catalyst at a temperature of from 250° to about 350° C., the improvement comprising homogeneously blending the methyl chloride and hydrogen chloride with an amount of gaseous hydrogen sufficient to reduce the concentration of methyltrichlorosilane in the product of said reaction.

2. A method according to claim 1 wherein hydrogen chloride and hydrogen each constitute from 0.01 up to 5 percent of the methyl chloride weight, the reaction between the methyl chloride and silicon is conducted at a temperature of from 260° to about 330° C. in the presence of a catalyst comprising copper or a copper compound and at least one member selected from the group consisting of tin, tin compounds, zinc and zinc compounds.

3. A method according to claim 2 where the concentration of copper is from 0.2 to 10 weight percent, the concentration of tin is from 5 to 200 ppm and the concentration of zinc is from 10 to 10,000 ppm, the concentrations being based on weight of initial reaction mass, and the combined yield of dimethyldichlorosilane and methyldichlorosilane is at least 85%.

4. A method according to claim 2 where the combined weight of hydrogen chloride and hydrogen constitute from 0.1 to 3 percent of the methyl chloride weight and hydrogen constitutes from 10 to 60 percent of the combined weight of hydrogen and hydrogen chloride and the reaction mass includes a catalyst/reaction promoter combination selected from the group consisting of
   copper or a copper compound and zinc or a zinc compound;
   copper or a copper compound and tin or a tin compound,
   copper or a copper compound, zinc or a zinc compound and tin or a tin compound;
   copper or a copper compound, tin or a tin compound, and arsenic or an arsenic compound, copper in the form of a mixture, alloy or compound, at least one member selected from the group consisting of tin, tin compounds, zinc and zinc compounds, and at least one member selected from the group consisting of phosphorus, phosphorus compounds, metal-phosphorus alloys, and metal phosphides;

copper or a copper compound, tin or a tin compound, arsenic or an arsenic compound, and phosphorus or a phosphorus compound;

copper or at least one copper compound and an alloy of silicon with either iron alone or an alloy of silicon, iron and aluminum;

(1) copper or at least one copper compound, (2) an alloy of silicon with either iron alone or an alloy of silicon, iron and aluminum, and (3) at least one member selected from the group consisting of tin, tin compounds, zinc, zinc compounds, elemental phosphorus, metal phosphides and metal-phosphorus alloys; and a mixture of copper and zinc that is present as brass, cuprous chloride, tin or at least one tin compound, and a metal-phosphorus alloy, where the concentrations of any iron and aluminum do not exceed one weight percent, based on the initial weight of silicon.

5. A method according to claim 4 where the metal portion of any metal-phosphorus alloy or phosphide is aluminum, calcium, copper, or zinc.

6. A method according to claim 2 where the reaction is conducted in a batch or semi-batch type reactor and hydrogen chloride is added during the initial 50 to 90% of the methyl chloride addition.

* * * * *